United States Patent [19]

Olson et al.

[11] 4,421,941

[45] Dec. 20, 1983

[54] CATALYST AND PROCESS FOR SELECTIVE PRODUCTION OF PARA-DIALKYSUBSTITUTED BENZENES

[75] Inventors: David H. Olson, Pennington; Paul G. Rodewald, Rocky Hill, both of N.J.

[73] Assignee: Mobil Oil Corporation, New York, N.Y.

[21] Appl. No.: 416,740

[22] Filed: Sep. 10, 1982

Related U.S. Application Data

[62] Division of Ser. No. 223,878, Jan. 8, 1981, Pat. No. 4,379,761.

[51] Int. Cl.$^3$ ............................................. C07C 2/68
[52] U.S. Cl. .................................. 585/467; 585/475
[58] Field of Search ............................... 585/467, 475

[56] References Cited

U.S. PATENT DOCUMENTS

| | | | |
|---|---|---|---|
| 2,904,607 | 9/1959 | Mattox et al. | 585/467 |
| 3,251,897 | 5/1966 | Wise | 585/455 |
| 3,446,645 | 5/1969 | Drost | 252/455 Z |
| 3,751,504 | 8/1973 | Keown et al. | 585/323 |
| 3,751,506 | 8/1973 | Burress et al. | 585/454 |
| 3,962,364 | 6/1976 | Young | 585/466 |
| 3,965,208 | 6/1976 | Butter et al. | 585/467 |
| 4,002,698 | 1/1977 | Kaeding | 585/467 |
| 4,016,219 | 4/1977 | Kaeding | 585/475 |
| 4,049,573 | 9/1977 | Kaeding | 252/437 |
| 4,086,287 | 4/1978 | Kaeding et al. | 585/467 |
| 4,088,605 | 5/1978 | Rollmann | 252/455 Z |
| 4,090,981 | 11/1978 | Rodewald | 252/455 Z |
| 4,127,616 | 5/1978 | Rodewald | 585/467 |

*Primary Examiner*—Curtis R. Davis
*Attorney, Agent, or Firm*—Michael G. Gilman; Charles J. Speciale; Van D. Harrison, Jr.

[57] ABSTRACT

Disclosed is a zeolite base catalyst useful particularly for the selective production of para-dialkylsubstituted benzene. The catalyst comprises a porous crystalline zeolite having silica deposited thereon and having incorporated therein phosphorous. Described also in the process for making the catalyst and the parameters for the use of the catalyst in dialkylation processes.

11 Claims, No Drawings

CATALYST AND PROCESS FOR SELECTIVE PRODUCTION OF PARA-DIALKYSUBSTITUTED BENZENES

This is a division of copending application Ser. No. 223,878, filed Jan. 8, 1981 now U.S. Pat. No. 4,379,761, issued Apr. 12, 1983.

BACKGROUND OF THE INVENTION

1. Field of the Invention

This invention relates to particular modified zeolite catalysts and their uses in the selective production of para-dialkylsubstituted benzenes and to a process for converting certain charge stocks to a high yield of para-dialkylsubstituted benzenes.

2. Description of the Prior Art

U.S. Pat. No. 2,904,607 refers to the alkylation of aromatic hydrocarbons with an olefin in the presence of a crystalline metallic aluminosilicate having uniform pore openings of about 6 to 15 Angstrom units. U.S. Pat. No. 3,251,897 describes alkylation of aromatic hydrocarbons in the presence of X- or Y-type crystalline aluminosilicate zeolites, specifically such type zeolites wherein the cation is rare earth and/or hydrogen. U.S. Pat. Nos. 3,751,504 and 3,751,506 describes vapor phase alkylation of aromatic hydrocarbons with olefins, e.g. benzene with ethylene, in the presence of a ZSM-5 type zeolite catalyst.

More recently, U.S. Pat. No. 4,090,981 has disclosed a catalyst particularly applicable for the selective production of para-dialkylsubstituted benzenes. It comprises a porous crystalline aluminosilicate zeolite having silica deposited on the surface thereof. U.S. Pat. No. 4,127,616 is directed to the process utilizing these zeolite compositions.

U.S. Pat. No. 3,962,364 describes the alkylation of aromatic compounds such as benzene and toluene with olefinic hydrocarbons, such as ethylene, utilizing zeolites (ZSM-5, ZSM-11, ZSM-35, etc.) which have been reacted with phosphorous compounds.

SUMMARY OF THE INVENTION

In one aspect, this invention constitutes a catalyst composition comprising a porous crystalline zeolite having silica deposited thereon. The silica-treated zeolite further contains phosphorous. In another aspect this invention comprises a process for making the catalyst composition of this invention comprising the steps of: impregnating a zeolite material with a solution of a silicon compound, calcining the resultant product, further impregnating the calcined product with a thermally decomposable phosphorous compound and subsequently calcining this product. In still another aspect, this invention constitutes the process for making para-dialkylated aromatic compound comprising reacting an olefinic compound and a substituted or unsubstituted aromatic compound in the presence of the catalyst of this invention under suitable conditions to effect dialkylation.

DETAILED DESCRIPTION OF THE INVENTION

The zeolite base component of the present catalyst upon which silica deposition is effected and in which phosphorous is incorporated is characterized by particular activity and sorption properties. Thus, the porous crystalline zeolite employed herein necessarily has: (1) an activity, in terms of alpha value, of between 2 and about 5000, (2) a xylene sorption capacity greater than 1 gram/100 grams of zeolite and (3) an ortho-xylene sorption time for 30 percent of said capacity of greater than 10 minutes, where the sorption capacity and sorption time are measured at 120° C. (248° F.) and a xylene pressure of 4.5±0.8 mm of mercury.

The alpha value reflects the relative activity of the catalyst with respect to a silica-alumina cracking catalyst. To determine the alpha value as such term is used herein, n-hexane conversion is determined at about 538° C. (1000° F.). Conversion is varied by varying the space velocity such that a conversion level of 10 to 60 percent of n-hexane is obtained and converted to a rate constant per unit volume of zeolite and compared with that of silica-alumina catalyst which is normalized to a reference activity of 538° C. (1000° F.). Catalytic activity of the catalysts is expressed as a multiple of this standard, i.e. the silica-alumina standard. The silica-alumina reference catalyst contains about 10 weight percent $Al_2O_3$ with the remainder $SiO_2$. This method of determining alpha, modified as described above, is more fully described in the Journal of Catalysis, Vol. VI, Pages 278–287, 1966.

The measurements of hydrocarbon sorption capacities and rates are conveniently carried out gravimetrically on a thermal balance. In particular, it has been found that an equilibrium sorption capacity of xylene, which can be either para, meta, ortho or a mixture thereof, preferably para-xylene since this isomer reaches equilibrium within the shortest time, of at least 1 gram per 100 grams of zeolite measured at 120° C. and a xylene pressure of 4.5±0.8 mm of mercury and an ortho-xylene sorption time for 30 percent of said capacity of greater than 10 minutes (at the same conditions of temperature and pressure) are required in order to achieve the desired selective production of para dialkyl substituted benzenes.

It has been found that zeolites exhibiting very high selectivity for para-dialkylbenzene production require a very long time, up to and exceeding a thousand minutes, to sorb ortho-xylene in an amount of 30% of total xylene sorption capacity. For those materials it is more convenient to determine the sorption time for a lower extent of sorption, such as 5%, 10% or 20% of capacity, and to estimate the 30% sorption time applying the following multiplication factors F as illustrated for 5% sorption thus:

| $t_{0.3} = (F) \times (t_{0.05})$ Percent of sorption capacity | Factor (F) to Estimate 30% Sorption Time |
|---|---|
| 5 | 36 |
| 10 | 9 |
| 20 | 2.2 |

Zeolites such as zeolites X, zeolite Y, ZSM-4, faujasite, mordenite, ferrierite and offretite which satisfy the aforementioned activity and sorption characteristics are within the confines of this invention. Particularly preferred are zeolites having a silica to alumina ratio of at least about 12 and a constraint index within the approximate range of 1 to 12, such as ZSM-5, ZSM-11, ZSM-12, ZSM-35, ZSM-38. These zeolites induce profound transformation of aliphatic hydrocarbons to aromatic hydrocarbons in commercially desirable yields and are generally highly effective in conversion reactions involving aromatic hydrocarbons.

Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this novel class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina mole ratio of at least 12 are useful, it is preferred in some instances to use zeolites having substantially higher silica/alumina ratios, e.g. 1600 and above. In addition, zeolites as otherwise characterized herein but which are substantially free of aluminum, that is zeolites having silica to alumina mole ratios of up to infinity, are found to be useful and even preferable in some instances. Such "high silica" or "highly siliceous" zeolites are intended to be included within this description. Also to be included within this definition are substantially pure silica analogs of the useful zeolites described herein, that is to say those zeolites having no measurable amount of aluminum (silica to alumina mole ratio of infinity) but which otherwise embody the characteristics disclosed.

The novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons and, therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

The "Constraint Index" is calculated as follows:

$$\frac{\text{Constraint}}{\text{Index}} = \frac{\log_{10} (\text{fraction of hexane remaining})}{\log_{10} (\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical materials are:

|        | C.I. |
|--------|------|
| ZSM-4  | 0.5  |
| ZSM-5  | 8.3  |
| ZSM-11 | 8.7  |
| ZSM-12 | 2    |
| ZSM-23 | 9.1  |
| ZSM-35 | 4.5  |
| ZSM-38 | 2    |

-continued

|  | C.I. |
|---|---|
| ZSM-48 | 3.4 |
| TMA Offretite | 3.7 |
| Clinoptilolite | 3.4 |
| Beta | 0.6 |
| H—Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Index. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The novel class of zeolites defined herein is exemplified by ZSM-5, ZSM-11, ZSM-12, ZSM-23, ZSM-35, ZSM-38, ZSM-48 and other similar materials.

ZSM-5 is described in greater detail in U.S. Pat. Nos. 3,702,886 and Re 29,948. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 can be identified, in terms of moles of anhydrous oxides per 100 moles of silica, as follows:

$$(0-15)RN:(0-1.5)M_{2/n}O:(0-2)Al_2O_3:(100)SiO_2$$

wherein:
M is at least one cation having a valence n; and
RN is a $C_1$-$C_{20}$ organic compound having at least one amine functional group of $pK_a \geq 7$.

It is recognized that, particularly when the composition contains tetrahedral, framework aluminum, a fraction of the amine functional groups may be protonated. The doubly protonated form, in conventional notation, would be $(RNH)_2O$ and is equivalent in stoichiometry to $2RN + H_2O$.

The characteristic X-ray diffraction pattern of the synthetic zeolite ZSM-48 has the following significant lines:

| Characteristic Lines of ZSM-48 | |
|---|---|
| d (Angstroms) | Relative Intensity |
| 11.9 | W-S |
| 10.2 | W |
| 7.2 | W |
| 5.9 | W |
| 4.2 | VS |
| 3.9 | VS |
| 3.6 | W |
| 2.85 | W |

These values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, 100 $I/I_o$, where $I_o$ is the intensity of the strongest line or peak, and d (obs.), the interplanar spacing in A, corresponding to the recorded lines, were calculated. In the foregoing table the relative intensities are given in terms of the symbols W=weak, VS=very strong and W-S=weak-to-strong. Ion exchange of the sodium with cations reveals substantially the same pattern with some minor shifts in interplanar spacing and variation in relative intensity. Other minor variations can occur depending on the silicon to aluminum ratio of the particular sample, as well as if it has been subjected to thermal treatment.

The ZSM-48 can be prepared from a reaction mixture containing a source of silica, water, RN, an alkali metal oxide (e.g. sodium) and optionally alumina. The reaction mixture should have a composition, in terms of mole ratios of oxides, falling within the following ranges:

| REACTANTS | BROAD | PREFERRED |
|---|---|---|
| $Al_2O_3/SiO_2 =$ | 0 to 0.02 | 0 to 0.01 |
| $Na/SiO_2 =$ | 0 to 2 | 0.1 to 1.0 |

| REACTANTS | BROAD | PREFERRED |
|---|---|---|
| $RN/SiO_2 =$ | 0.01 to 2.0 | 0.05 to 1.0 |
| $OH^-/SiO_2 =$ | 0 to 0.25 | 0 to 0.1 |
| $H_2O/SiO_2 =$ | 10 to 100 | 20 to 70 |
| $H^+(added)/SiO_2 =$ | 0 to 0.2 | 0 to 0.05 | wherein RN is a $C_1$-$C_{20}$ organic compound having amine functional group of $pK_a \geq 7$. The mixture is maintained at 80°–250° C. until crystals of the material are formed. $H^+$(added) is moles acid added in excess of the moles of hydroxide added. In calculating $H^+$(added) and OH values, the term acid ($H^+$) includes both hydronium ion, whether free or coordinated, and aluminum. Thus aluminum sulfate, for example, would be considered a mixture of aluminum oxide, sulfuric acid, and water. An amine hydrochloride would be a mixture of amine and HCl. In preparing the highly siliceous form of ZSM-48 no alumina is added. Thus, the only aluminum present occurs as an impurity in the reactants.

Preferably, crystallization is carried out under pressure in an autoclave or static bomb reactor at 80° C. to 250° C. Thereafter, the crystals are separated from the liquid and recovered. The composition can be prepared utilizing materials which supply the appropriate oxide. Such compositions include sodium silicate, silica hydrosol, silica gel, silicic acid, RN, sodium hydroxide, sodium chloride, aluminum sulfate, sodium aluminate, aluminum oxide, or aluminum itself. RN is a $C_1$-$C_{20}$ organic compound containing at least one amine functional group of $pK_a \geq 7$, as defined above, and includes such compounds as $C_3$-$C_{18}$ primary, secondary, and tertiary amines, cyclic amine (such as piperidine, pyrrolidine and piperazine), and polyamines such as $NH_2$—$C_nH_{2n}$—$NH_2$ wherein n is 4–12.

The original cations can be subsequently replaced, at least in part, by calcination and/or ion exchange with another cation. Thus, the original cations are exchanged into a hydrogen or hydrogen ion precursor form or a form in which the original cation has been replaced by a metal of Groups I through VIII of the Periodic Table. Thus, for example, it is contemplated to exchange the original cations with ammonium ions or with hydronium ions. Catalytically active forms of these would include, in particular, hydrogen, rare earth metals, aluminum, manganese and other metals of Groups I and VIII of the Periodic Table.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38, and ZSM-48, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article ZEOLITE STRUCTURE, by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In accordance with this invention, a porous crystalline zeolite, as above characterized, has silica deposited thereon and phosphorous incorporated therein. The silica is deposited on the zeolite by contacting the latter with a silicone compound of a molecular size incapable of entering the pores of the zeolite and by subsequently heating in an oxygen-containing atmosphere, such as air, to a temperature above 300° C. but below a temperature at which the crystallinity of the zeolite is adversely affected at a rate such that the silicone compound does not volatilize before undergoing oxidation to silica.

The silicone compound utilized to effect the silica deposition is characterized by the general formula:

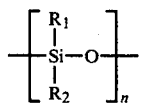

where $R_1$ is hydrogen, fluorine, hydroxy, alkyl, aralkyl, alkaryl or fluoro-alkyl. The hydrocarbon substituents generally contain from 1 to 10 carbon atoms and preferably are methyl or ethyl groups. $R_2$ is selected from the same group as $R_1$, other than hydrogen and n is an integer of at least 10 and generally in the range of 10 to 1000. The molecular weight of the silicone compound employed is generally between about 500 and about 20,000 and preferably within the approximate range of 1000 to 10,000. Representative silicone compounds include dimethylsilicone, diethylsilicone, phenylmethylsilicone, methylhydrogensilicone, ethylhydrogensilicone, phenylhydrogensilicone, methylethylsilicone, phenylethylsilicone, diphenylsilicone, methyltrifluoropropylsilicone, ethyltrifluoropropylsilicone, polydimethylsilicone, tetrachlorophenylmethylsilicone, tetrachlorophenylethyl silicone, tetrachlorophenylhydrogen silicone, tetrachlorophenylphenyl silicone, methylvinylsilicone and ethylvinylsilicone.

The silicone compound dissolved in a suitable solvent therefor, e.g., pentane, hexane, heptane, benzene, toluene, chloroform, carbon tetrachloride, is contacted with the above described zeolite at a temperature between about 10° C. and about 100° C. for a period of time sufficient to deposit the ultimately desired amount of silicone thereon. Time of contact will generally be within the range of 0.2 to 5 hours, during which time the mixture is desirably subjected to evaporation. The resulting residue is then calcined in an oxygen-containing atmosphere, preferably air, at a rate of 0.2° to 5° C./minute to a temperature greater than 200° C. but below a temperature at which the crystallinity of the zeolite is adversely affected. Generally, such temperature will be below 600° C. Preferably the temperature of calcination is within the approximate range of 350° to 550° C. The product is maintained at the calcination temperature usually for 1 to 24 hour to yield a zeolite composition containing between about 0.5 and about 30 weight percent and preferably between about 1 and 15 weight percent of silica.

The calcined product thus obtained is then contacted with a phosphorous compound. Representative phosphorous-containing compounds include derivatives of groups represented by $PX_3$, $RPX_2$, $R_2PX$, $R_3P$, $X_3PO$, $(XO)_3PO$, $(XO)_3P$, $R_3P{=}O$, $R_3P{=}S$, $RPO_2$, $PPS_2$, $RP(O)(OX)_2$, $RP(S)(SX)_2$, $R_2P(O)(OX)$, $R_2P(S)SX$, $RP(OX)_2$, $RP(Sx)_2ROP(OX)_2$, $RSP(SX)_2$, $(RS)_2PSP(SR)_2$, and $(RO)_2POP(OR)_2$, where R is an alkyl or aryl, such as phenyl and X is hydrogen, R or halide. These compounds include primary, $RPH_2$, secondary, $R_2PH$ and tertiary, $R_3P$, phosphines such as butyl phosphine; the tertiary phosphine oxides $R_3PO$, such as tributylphosphine oxide, the tertiary phosphine sulfides, $R_2PS$, the primary $RP(O)(OX)_2$, and secondary, $R_2P(O)(OX)$, phosphonic acids such as benzene phosphonic acid; the corresponding sulfur derivatives such as $RP(S)(SX)_2$ and $R_2P(S)SX$, the esters of the phosphonic acids such as diethyl phosphonate, $(RO)_2P(O)H$, dialkyl alkyl phosphonates, $(RO)_2P(O)R$, and alkyl dialkylphosphinates, $(RO)P(O)R_2$, phosphinous acids, $R_2POX$, such as diethylphosphinous acid, primary, $(RO)P(OX)_2$, secondary, $(RO)_2POX$, and tertiary, $(RO)_3P$, phosphites; and esters thereof such as the monopropyl ester, alkyl dialkylphosphinites, $(RO)PR_2$, and dialkyl alkyl phosphonites, $(RO)_2PR$ esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$ and $(RS)_2PR$. Examples of phosphite esters include trimethylphosphite, triethylphosphite, diisopropylphosphite, butylphosphite; and pyrophosphites such as tetraethylpyrophosphite. The alkyl groups in the mentioned compounds contain 1 to 4 carbon atoms.

Other suitable phosphorous-containing compounds include the phosphorus halides such as phosphorus trichloride, bromide, and iodide, alkyl phosphorodichloridites, $(RO)PCl_2$, dialkyl phosphorochloridites, $(RO)_2PX$, dialkylphosphinochloridites, $R_2PCl$, alkyl alkylphosphonochloridates, (RO)(R)P(O)Cl, dialkyl phosphinochloridates, R$_2$P(O)Cl and RP(O)Cl$_2$. Applicable corresponding sulfur derivatives include (RS)PCl$_2$, (RS)$_2$PX, (RS)(R)P(S)Cl and R$_2$P(S)Cl.

Preferred phosphorous-containing compounds include monobasic and dibasic ammonium phosphates diphenyl phosphine chloride, trimethylphosphite and phosphorus trichloride, phosphoric acid, phenyl phosphine oxychloride, trimethylphosphate, diphenyl phosphinous acid, diphenyl phosphinic acid, diethylchloro thiophosphate, methyl acid phosphate and other reaction products.

Reaction with the phosphorus compound of the product resulting from depositing silica on the zeolite and calcining it is effected by contacting the calcined product with such compound. Where the treating phosphorus compound is a liquid, such compound can be in solution in a solvent at the time contact with the zeolite is effected. Any solvent relatively inert with respect to the treating compound and the zeolite may be employed. Suitable solvents include water and aliphatic, aromatic or alcoholic liquids. Where the phosphorus-containing compound is, for example, trimethylphosphite or liquid phosphorus trichloride, a hydrocarbon solvent such as n-octane may be employed. The phosphorus-containing compound may be used without a solvent, i.e., may be used as a neat liquid. Where the phosphorus-containing compound is in the gaseous phase, such as where gaseous phosphorus trichloride is employed, the treating compound can be used by itself or can be used in admixture with a gaseous diluent relatively inert to the phosphorus-containing compound and the zeolite-silica coated product such as air or nitrogen or with an organic solvent, such as octane or toluene.

Heating of the phosphorus-containing silica-treated zeolite catalyst subsequent to preparation and prior to use is also preferred. The heating can be carried out in the presence of oxygen, for example air. Heating can be at a temperature of about 150° C. However, higher temperatures, i.e., up to about 500° C., are preferred. Heating is generally carried out for 3–5 hours but may be extended to 24 hours or longer. While heating temperatures above about 500° C. can be employed, they are not necessary. At temperatures of about 1000° C., the crystal structure of the zeolite tends to deteriorate.

The amount of phosphorus incorporated with the zeolite should be at least about 0.5 percent by weight. The amount of phosphorus can be as high as about 25 percent by weight or more depending on the amount and type of binder present.

The amount of phosphorus incorporated with the silica-treated zeolite by reaction with the phosphorus-containing compound will depend upon several factors. One of these is the reaction time, i.e., the time that the zeolite and the phosphorus-containing source are maintained in contact with each other. With greater reaction times, all other factors being equal, a greater amount of phosphorus is incorporated with the zeolite. Other factors upon which the amount of phosphorus incorporated with the zeolite is dependent include reaction temperature, concentration of the treating compound in the reaction mixture, the degree to which the zeolite has been dried prior to reaction with the phosphorus-containing compound, the conditions of drying of the zeolite after reaction of the zeolite with the treating compound, and the amount and type of binder incorporated with the zeolite.

In practicing a particularly desired chemical conversion process, it may be useful to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in many cracking processes.

Useful matrix materials include both synthetic and naturally occurring substances, as well as inorganic materials such as clay and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the phosphorus-containing zeolites having a silica deposit thereon employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

The charge stock used herein for the selective production of para dialkyl substituted benzenes containing alkyl groups of 1 to 4 carbon atoms by contact, under conversion conditions, with the above-described catalyst includes a hydrocarbon precursor selected from the group consisting of mono alkylsubstituted benzenes having 1–4 carbon atoms in the alkyl-substituent, such as toluene, ethyl benzene, propyl benzene or butyl benzene and a mixture of such precursor or benzene with an alkylating agent containing from 1 to 4 carbon atoms.

Typical of the processes contemplated herein are disproportionation of toluene to benzene and xylene, wherein the proportion of para-xylene obtained is greatly in excess of its normal equilibrium concentration. Such process is effectively carried out at a temperature of between about 400° C. and about 700° C. at a pressure between 1 and about 100 atmospheres utilizing a weight hourly space velocity of between about 1 and about 50.

The use of mixed aromatics as feed is also feasible. For example, a mixture of ethylbenzene and toluene is converted selectively to a mixture rich in p-diethylbenzene and p-ethyltoluene, the latter predominating at high toluene to ethylbenzene ratios in the feed.

Reaction of benzene, toluene, ethylbenzene, propylbenzene or butylbenzene with an alkylating agent containing from 1 to 4 carbon atoms is also contemplated using the catalyst described hereinabove. Suitable alkylating agents include olefins, alcohols, alkyl halides, ethers, sulfides having from 1 to 4 carbon atoms. Representative of such compounds are ethylene, propylene, butylene, methanol, ethanol, propanol, butanol, methyl chloride, ethyl chloride, propyl chloride, butyl chloride, dimethylether, dimethylsulfide, diethylether, diethylsulfide, dipropylether, dipropylsulfide, dibutylether and dibutylsulfide. Alkylation is suitably carried out at a temperature between about 250° C. and about 700° C. at a pressure between about 1 atmosphere and about 100 atmospheres employing a weight hourly spaced velocity of between about 0.1 and about 200.

It is contemplated that the conversion process described herein may be carried out as a batch type, semi-continuous or continuous operation utilizing a fixed or moving bed catalyst system. The catalyst after use is conducted to a regeneration zone wherein coke is burned from the catalyst in an oxygen-containing atmosphere, e.g. air, at an elevated temperature, after which the regenerated catalyst is recycled to the conversion zone for further contact with the charge stock. With use of the present silica-coated zeolite catalyst, regeneration has been found to restore the activity of the catalyst to a high level, thereby providing a long catalyst life. It is particularly feasible to conduct the desired conversion in the presence of hydrogen utilizing a hydrogen/hydrocarbon mole ratio of between about 2 and about 20, with hydrogen pressure extending up to 100 atmospheres. The presence of hydrogen in the reaction zone has been found to very substantially reduce the aging rate of the catalyst.

While the above process has been described with reference to selective production of para dimethyl substituted benzenes, typified by para-xylene, it is contemplated that other para dialkyl substituted benzenes, wherein the alkyl group contains from 1 to 4 carbon atoms may similarly be selectively produced. Thus, utilizing the technique described herein, it is contemplated that with selection of a suitable precursor, a mixture of ethyl benzene and toluene may be selectively converted to para ethyl toluene; ethyl benzene may be selectively converted to para diethyl benzene, propyl benzene may be converted to dipropyl benzene and butyl benzene may be selectively converted to dibutylbenzenes.

The following examples will serve to illustrate the process and catalyst of the present invention without limiting the same.

EXAMPLE 1

To 0.51 grams of phenylmethylsilicone (molecular weight 1686) dissolved in 20 cc of n-hexane was added 2.0 grams of NH$_4$ZSM-5 having a crystallite size of approximately 0.5-4 microns. The mixture was then evaporated using a rotary evaporator. The residue was heated in an oil bath for 1 hour at a temperature of 100° C. (212° F.) and was then calcined in air at 1° C. per minute to 538+ C. (1000° F.) and then maintained at this temperature for 7 hours.

Toluene, ethylene and hydrogen in a molar ratio of 8:1:3 respectively were passed over a portion of this catalyst at conditions of 385° C. (725° F.), 790 R Pa (100 psig), and WHSV of 29. After 4.3 hours of this test had elapsed, analysis of the produced product showed a 96% consumption of ethylene. The concentration in the effluent of para-ethyltoluene was 88 mole percent and that of ortho-ethyltoluene 0.33 mole percent. After 24.5 hours of the test, the ethylene consumption was 95% and the amounts of para-ethyltoluene and ortho-ethyltoluene produced were 92% and 0.26% respectively.

EXAMPLE 2

To 21.4 grams of the catalyst prepared in Example 1 40 cc of 10% solution of diammonium phosphate was added and maintained in contact for 2 hours. The solution was decanted from the catalyst material and the resulting catalyst product was then calcined in air at an increasing temperature of 1° C. per minute until a temperature of 538° C. (1000° F.) was achieved. The catalyst was further calcined at a constant temperature of 538° C. over a period of 7 hours.

This catalyst was then tested under conditions identical to those in Example 1. At the end of 2.2 hours analysis indicated the rate of ethylene consumption was 85% and the concentrations of para-ethyltoluene and ortho-ethyltoluene in the effluent product stream were 97% and 0.06% respectively. This latter test thus shows a substantial increase in the production of the desired para-ethyltoluene and a substantial decrease in the production of the undesired ortho-ethltoluene.

We claim:

1. A process for the selective production of para dialkyl substituted benzenes wherein the alkyl group contains from 1 to 4 carbon atoms which comprises contacting, under conversion conditions, a hydrocarbon precursor selected from the group consisting of mono alkyl-substituted benzenes having 1-4 carbon atoms in the alkyl substituent and a mixture of said precursor or benzene with an alkylation agent containing from 1 to 4 carbon atoms with a catalyst composition comprising a porous crystalline zeolite, having silica deposited thereon as a result of contact with a silicone compound of a molecular size incapable of entering the pores of the zeolite and subsequent heating in an oxygen-containing atmosphere to a temperature in excess of 300° C. but below a temperature at which crystallinity of the zeolite is adversely affected at a rate such that the silicone compound does not volatilize being characterized by an activity, in terms of alpha value, of between about 2 and about 5000, a xylene sorption capacity greater than 1 gram/100 grams of zeolite and an ortho xylene sorption time for 30 percent of said capacity greater than 10 minutes, said sorption capacity and sorption time being measured at 120° C. and a pressure of 4.5±0.8 mm. of mercury and modified by the addition thereto of phosphorus, and recovering from the resulting product mixture, a para-dialkyl-substituted benzene in an amount greater than the thermodynamic equilibrium concentration thereof in the total dialkyl substituted benzenes produced.

2. The process of claim 1 wherein said conversion conditions include a temperature between about 250° and about 750° C., a pressure between about 0.1 atmosphere and about 100 atmospheres utilizing a weight hourly space velocity of between about 0.1 and about 2000.

3. The process of claim 1 wherein toluene is disproportioned.

4. The process of claim 3 wherein said conversion conditions include a temperature between about 400° and about 700° C. at a pressure between about 1 atmosphere and about 100 atmospheres and a weight hourly space velocity of between about 1 and about 50.

5. The process of claim 1 wherein the para dialkyl substituted benzene is para-xylene.

6. The process of claim 1 wherein the para dialkyl substituted benzene is para-ethyltoluene.

7. The process of claim 1 wherein said crystalline aluminosilicate zeolite is ZSM-5.

8. The process of claim 1 wherein toluene is alkylated with an alkylating agent containing from 1 to 4 carbon atoms.

9. The process of claim 8 wherein said crystalline zeolite is ZSM-5.

10. The process of claim 1 wherein said alkylating agent is ethylene.

11. The process of claim 1 wherein said conversion conditions include a temperature between about 250° and about 700° C., a pressure between about 1 and about 100 atmospheres utilizing a weight hourly space velocity of between about 0.1 and about 200.

* * * * *